United States Patent [19]
Horiuchi

[11] Patent Number: 6,067,341
[45] Date of Patent: May 23, 2000

[54] X-RAY COMPUTED TOMOGRAPHY METHOD AND APPARATUS

[75] Inventor: Tetsuya Horiuchi, Tokyo, Japan

[73] Assignee: GE Yokogawa Medical Systems, Limited

[21] Appl. No.: 09/158,032

[22] Filed: Sep. 22, 1998

[30] Foreign Application Priority Data

Sep. 30, 1997 [JP] Japan ................................. 9-266220

[51] Int. Cl.[7] ...................................................... A61B 6/00
[52] U.S. Cl. ................... 378/8; 378/4; 378/901
[58] Field of Search .................. 378/4, 8, 901

[56] References Cited

U.S. PATENT DOCUMENTS

| | | | |
|---|---|---|---|
| 5,103,469 | 4/1992 | Tanaka | 378/16 |
| 5,379,333 | 1/1995 | Toth | 378/16 |
| 5,400,378 | 3/1995 | Toth | 378/16 |
| 5,696,807 | 12/1997 | Hsieh | 378/109 |

FOREIGN PATENT DOCUMENTS 1293844  11/1989  Japan .

*Primary Examiner*—David V. Bruce
*Assistant Examiner*—Allen C. Ho
*Attorney, Agent, or Firm*—Moonray Kojima

[57] ABSTRACT

In order for image data pixel value ranges for several slices to be contained within the same preferred range, an x-ray computed tomography method and apparatus comprises an x-ray source 2 for emitting x-rays toward a subject, an x-ray detector 3 for detecting subject transmission information of the emitted x-rays and control means 15 for controlling the x-ray emission and detection, wherein the control means exerts the control so as to, prior to the tomographic imaging of the subject, produce scout images by fixing the angular position of the x-ray source at two different angular positions and performing the scout imaging of the subject respectively at the angular positions; calculates a scanning condition with reference to the standard deviation of image data based on the area of projection display data, a desired standard deviation of the image data and the pixel value attenuation ratio between the scout images acquired respectively at the two angular positions of the x-ray source; and exerts the control so as to perform the tomographic imaging according to the scanning condition.

4 Claims, 3 Drawing Sheets

X-RAY COMPUTED TOMOGRAPHY METHOD AND APPARATUS

BACKGROUND OF THE INVENTION

The present invention relates to an x-ray computed tomography (CT) method and apparatus, and more particularly, to an x-ray computed tomography method and apparatus which is arranged to contain image data pixel value ranges for several slices within the same preferred range.

In conventional x-ray computed tomography apparatuses, a fan-shaped x-ray beam emitted from an x-ray source impinges upon a subject, and the transmitted x-rays are measured by a one-dimensional array of x-ray detector elements consisting of a plurality of detector elements arranged along the extent of the fan-shaped x-ray beam.

The transmitted x-rays are measured in a plurality of view directions while the x-ray source and the detector element array are rotated around the subject. This procedure for measuring the transmitted x-rays is referred to as "scanning". Based on the measured data for the plurality of views acquired by the scanning, a tomographic image of the subject is reconstructed.

When image data of the tomographic image of the subject thus produced is displayed on a image display device such as a CRT (cathode ray tube) display, pixel values in the image data (i.e., CT values in the case of the x-ray computed tomography apparatus) are determined according to the transmission factor of the x-ray, and generally defined such that the air has a value of −1,000 and the water has a value of 0.

The image is displayed by converting such image data pixel values into display data having gradations of the order of 256. Although the number of the gradations of the display data varies with the image display circuit or circuit configuration of the CRT display device, it is generally of the order of 256 (the intensity data is processed in 8-bit), and it is not practical to provide a wide range of gradation for display, such as those having the image data pixel value ranging from −1,000 to +2,000.

For example, consider the case in which the internal organs of the subject to be observed give the pixel value ranging between −150 and +150 in CT value. In this case, the concept of "window width" is introduced. The display data is converted to display a range corresponding to the window width with 256 gradations. The image is displayed with shading, in which the portion having a CT value above the upper limit is represented in white or black and the portion having a CT value below the lower limit is represented in black or white. This procedure can adapt the image data of the region which is to be observed to be contained within the displayable gradation range, and the image data can be displayed as varying contrast.

Prior to the tomographic imaging, scout scanning is sometimes performed to determine preferred imaging positions. In the scout scanning, while translating the table plate on which the subject is rested with the x-ray tube and the x-ray detector fixed, the subject is irradiated with x-rays to obtain an x-ray visualized image.

Japanese Patent Application Laid Open No. 1-293844 (1989) discloses a technique in which an x-ray dose as a scanning condition is determined by estimating the x-ray attenuation relative to the average detected value of the transmitted x-rays during the scout scanning.

Since the body shapes of several subjects are unequal, however, it is difficult to determine the optimum scanning condition from the detected value in the scout scanning performed at a single angular position of the x-ray source.

Moreover, since the cross-sectional shape of a subject varies from slice to slice, the dispersion in pixel value range of the obtained image data occurs between the slices. This poses a problem that the respective pixel value ranges of the image data acquired from several slices are different from slice to slice.

SUMMARY OF THE INVENTION

It is an object of the present invention to provide an x-ray computed tomography (CT) method and apparatus in which image data pixel value ranges for several slices can be contained within the same preferred range.

The invention as solving means for the problem will now be described.

(1) In accordance with a first aspect, the present invention provides an x-ray computed tomography method in which x-rays emitted from an x-ray source impinges upon a subject placed within a measured volume and the transmitted x-rays are detected by an array of x-ray detector elements, the method comprising the steps of: prior to the tomographic imaging of the subject, producing scout images by fixing the angular position of the x-ray source at two different angular positions and performing the scout imaging of the subject respectively at the angular positions; calculating a scanning condition with reference to the standard deviation of image data based on the area of projection display data, a desired standard deviation of the image data and the pixel value attenuation ratio between the scout images acquired respectively at the two angular positions of the x-ray source; and performing the tomographic imaging of the subject according to the scanning condition.

In the invention according to the first aspect, the standard deviation $\sigma$ of the image data based on the area of the projection display data, and the pixel value attenuation ratio between the scout images acquired respectively at the two angular positions of the x-ray source give the standard deviation $\sigma'$ of the image data under the scanning condition 'default_mAs' prescribed as a default value. And the standard deviation $\sigma'$ and a desired standard deviation $\sigma_{target}$ give a scanning condition 'scan_mAs' required to attain the desired standard deviation. The tomographic imaging of the subject is performed according to the scanning condition thus obtained.

As a result, the scanning condition for each slice can be controlled so that the standard deviation of the image data is equal to $\sigma_{target}$, which enables the ranges of dispersion in pixel value for several slices to be contained within the same preferred range.

(2) In accordance with a second aspect, the present invention provides an x-ray computed tomography apparatus comprising an x-ray source for emitting x-rays toward a subject, an x-ray detector for detecting subject transmission information of the emitted x-rays and control means for controlling the x-ray emission and detection, wherein the control means exerts the control so as to, prior to the tomographic imaging of the subject, produce scout images by fixing the angular position of the x-ray source at two different angular positions and performing the scout imaging of the subject respectively at the angular positions; calculates a scanning condition with reference to the standard deviation of image data based on the area of projection display data, a desired standard deviation of the image data and the pixel value attenuation ratio between the scout images acquired respectively at the two angular positions of the x-ray source; and exerts the control so as to perform the tomographic imaging of the subject according to the scanning condition.

In the invention according the second aspect, through the function of the control means, the standard deviation σ of the image data based on the area of the projection display data, and the pixel value attenuation ratio between the scout images acquired respectively at the two angular positions of the x-ray source give the standard deviation σ' of the image data under the scanning condition 'default_mAs' prescribed as a default value. And the standard deviation σ' and a desired standard deviation $σ_{target}$ give a scanning condition 'scan_mAs' required to attain the desired standard deviation. The tomographic imaging of the subject is performed according to the scanning condition thus obtained.

As a result, the scanning condition for each slice can be controlled so that the standard deviation of the image data is equal to $σ_{target}$, which enables the ranges of dispersion in pixel value for several slices to be contained within the same preferred range.

(3) In accordance with a third aspect, the present invention provides the x-ray computed tomography apparatus as described regarding the second aspect, wherein the control means fixes the x-ray source at angular positions so that the respective maximum pixel values in the scout images acquired respectively at the angular positions of the x-ray source are expected to be the largest and smallest values.

In the invention according to the third aspect, for the scout images taken in two directions for use in determining the scanning condition, since the directions of scout imaging in which the respective maximum pixel values in the scout images are expected to be the largest and smallest values are selected as the x-ray source emitting direction, the standard deviation σ' of the image data for the actual subject can be accurately calculated using the standard deviation σ of the image data based on the area of the projection display data, and the attenuation ratio.

As a result, the scanning condition for each slice can be controlled so that the standard deviation of the image data is equal to a desired value, which enables the ranges of dispersion in pixel value for several slices to be contained within the same preferred range.

(4) In accordance with a fourth aspect, the present invention provides the x-ray computed tomography apparatus as described regarding the third aspect, wherein one of the angular positions of the x-ray source at which the maximum pixel value of the scout image is the largest value is selected to be in a direction parallel to the sagittal plane, and the other of the angular positions of the x-ray source at which the maximum pixel value of the scout image is the smallest value is selected to be in a direction parallel to the coronal plane.

In the invention according to the fourth aspect, for the scout images taken in two directions for use in determining the scanning condition, since the two directions of scout imaging are selected to be the sagittal and coronal directions in which the respective maximum pixel values in the scout images are expected to be the largest and smallest values, the standard deviation σ' of the image data for the actual subject can be accurately calculated using the standard deviation σ of the image data based on the area of the projection display data, and the attenuation ratio.

As a result, the scanning condition for each slice can be controlled so that the standard deviation of the image data is equal to a desired value, which enables the ranges of dispersion in pixel value for several slices to be contained within the same preferred range.

That is, the present invention offers the following effects.

(1) In the invention of the x-ray computed tomography method according to the first aspect, the standard deviation σ of the image data based on the area of the projection display data, and the pixel value attenuation ratio between the scout images acquired respectively at the two angular positions of the x-ray source give the standard deviation σ' of the image data under the scanning condition 'default_mAs' prescribed as a default value. And the standard deviation σ and a desired standard deviation $σ_{target}$ give a scanning condition 'scan_mAs' required to attain the desired standard deviation. The tomographic imaging of the subject is performed according to the scanning condition thus obtained.

As a result, the scanning condition for each slice can be controlled so that the standard deviation of the image data is equal to $σ_{target}$, which enables the ranges of dispersion in pixel value for several slices to be contained within the same preferred range.

(2) In the invention of the x-ray computed tomography apparatus according the second aspect, through the function of the control means, the standard deviation σ of the image data based on the area of the projection display data, and the pixel value attenuation ratio between the scout images acquired respectively at the two angular positions of the x-ray source give the standard deviation σ' of the image data under the scanning condition 'default_mAs' prescribed as a default value. And the standard deviation σ and a desired standard deviation $σ_{target}$ give a scanning condition 'scan_mAs' required to attain the desired standard deviation. The tomographic imaging of the subject is performed according to the scanning condition thus obtained.

As a result, the scanning condition for each slice can be controlled so that the standard deviation of the image data is equal to $σ_{target}$, which enables the ranges of dispersion in pixel value for several slices to be contained within the same preferred range.

(3) In the invention of the x-ray computed tomography apparatus according to the third aspect, for the scout images taken in two directions for use in determining the scanning condition, since the directions of scout imaging in which the respective maximum pixel values in the scout images are expected to be the largest and smallest values are selected as the x-ray source emitting direction, the standard deviation σ' of the image data for the actual subject can be accurately calculated using the standard deviation σ of the image data based on the area of the projection display data, and the attenuation ratio.

As a result, the scanning condition for each slice can be controlled so that the standard deviation of the image data is equal to a desired value, which enables the ranges of dispersion in pixel value for several slices to be contained within the same preferred range.

(4) In the invention of the x-ray computed tomography apparatus according to the fourth aspect, for the scout images taken in two directions for use in determining the scanning condition, since the two directions of scout imaging are selected to be the sagittal and coronal directions in which the respective maximum pixel values in the scout images are expected to be the largest and smallest values, the standard deviation σ of the image data for the actual subject can be accurately calculated using the standard deviation σ of the image data based on the area of the projection display data, and the attenuation ratio.

As a result, the scanning condition for each slice can be controlled so that the standard deviation of the image data is equal to a desired value, which enables the ranges of dispersion in pixel value for several slices to be contained within the same preferred range.

Further objects and advantages of the present invention will be apparent from the following description of the preferred embodiments of the invention as illustrated in the accompanying drawings.

DETAILED DESCRIPTION OF THE INVENTION

Some preferred embodiments of the present invention will now be described in more detail with reference to the accompanying drawings.

<Configuration of an X-ray Computed Tomography Apparatus>

Figure 2:
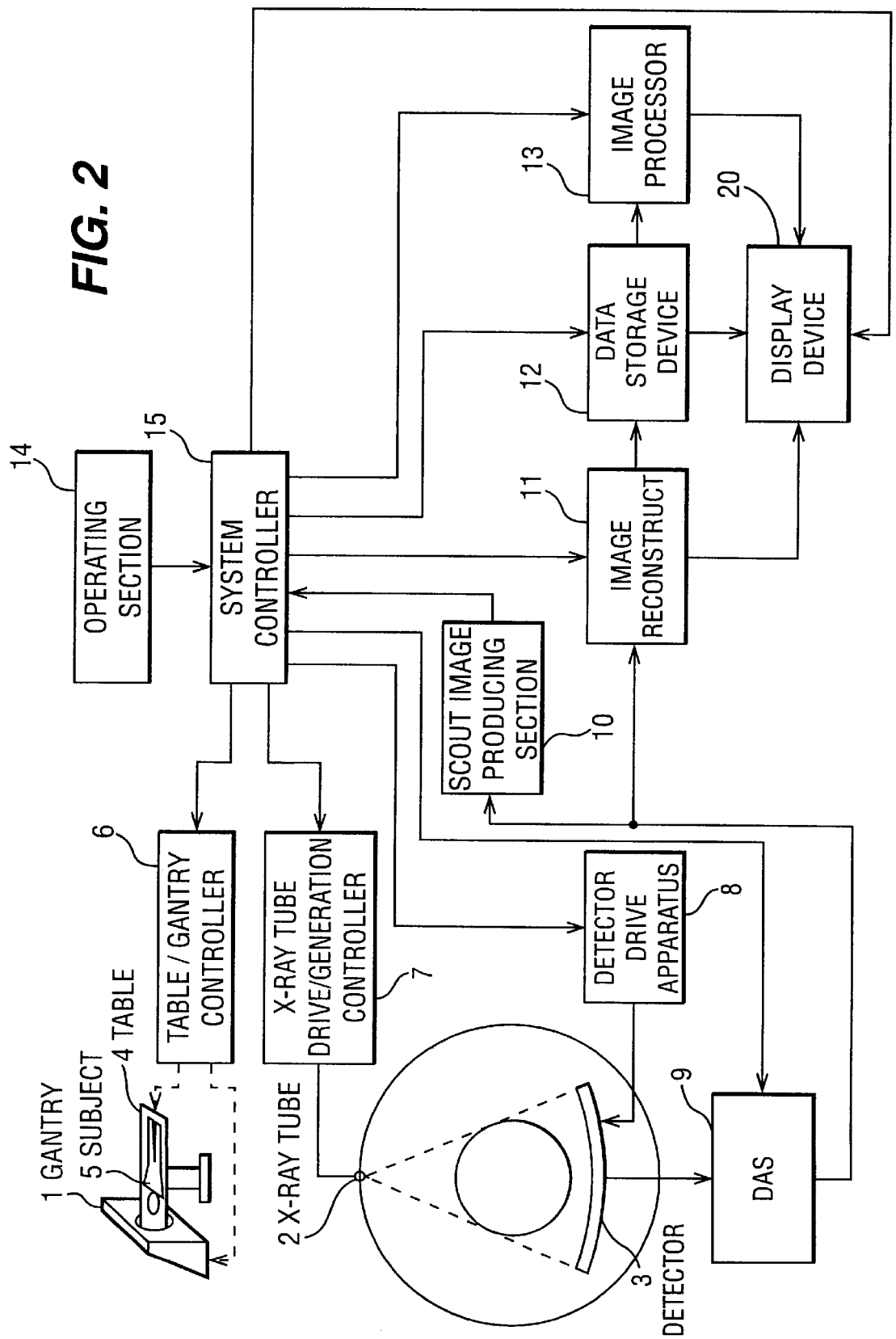
FIG. 2 is a block diagram illustrating the configuration which employs an x-ray computed tomography apparatus in accordance with one embodiment of the present invention.

Overall configuration of an x-ray computed tomography apparatus utilizing an x-ray CT scanner will be described with reference to FIG. 2.

A gantry 1 is a mechanical portion of the x-ray CT scanner in which an x-ray tube 2 and a detector 3 mechanically or electrically operate around a subject according to several scanning techniques.

A table 4 is fed into the gantry 1 with a subject 5 rested thereon. The tilt of the gantry 1 and the movement of the table 4 etc. are controlled by a table/gantry controller 6.

The x-ray tube 2 is controlled by an x-ray tube drive/generation controller 7 to rotate or stop, and to generate x-rays or terminate the generation. The table/gantry controller 6 and a system controller which will be described later constitute drive control means.

The detector 3 rotates with the x-ray tube 2 around the subject 5 under the control of a detector drive apparatus 8.

Upon emission by the x-ray tube 2, the x-rays transmit through the subject 5 and are detected by the detector 3, and their data are acquired by a data acquisition system (DAS) 9. The acquired data is transferred to a scout image producing section 10 and an image reconstructor 11.

The scout image producing section 10 produces a scout image from subject transmission projection data obtained by scout imaging. The scout image is used to determine the scanning positions and the scanning conditions.

The image reconstructor 11 performs the image reconstruction on the supplied data to produce image data, displays the image data on a display device 20 and simultaneously stores the image data in a data storage device 12.

The image data stored in the data storage device 12 is read out to produce a projection image in an image processor 13, as will be described later, and the projection image is displayed on the display device 20.

An operating section 14 is input means from which several commands are input. The system controller 15 controls the entire system according to the commands supplied from the operating section 14 and the predetermined operation program and scanning plan.

<X-ray Computed Tomography Method>

An X-ray computed tomography method executed by the above-described x-ray computed tomography apparatus will now be described with reference to a flow chart shown in FIG. 1.

[Production of a Scout Image]

Prior to performing the tomographic imaging on the subject 5, the scout imaging is first performed on the subject 5 from a plurality of directions.

Figure 1:
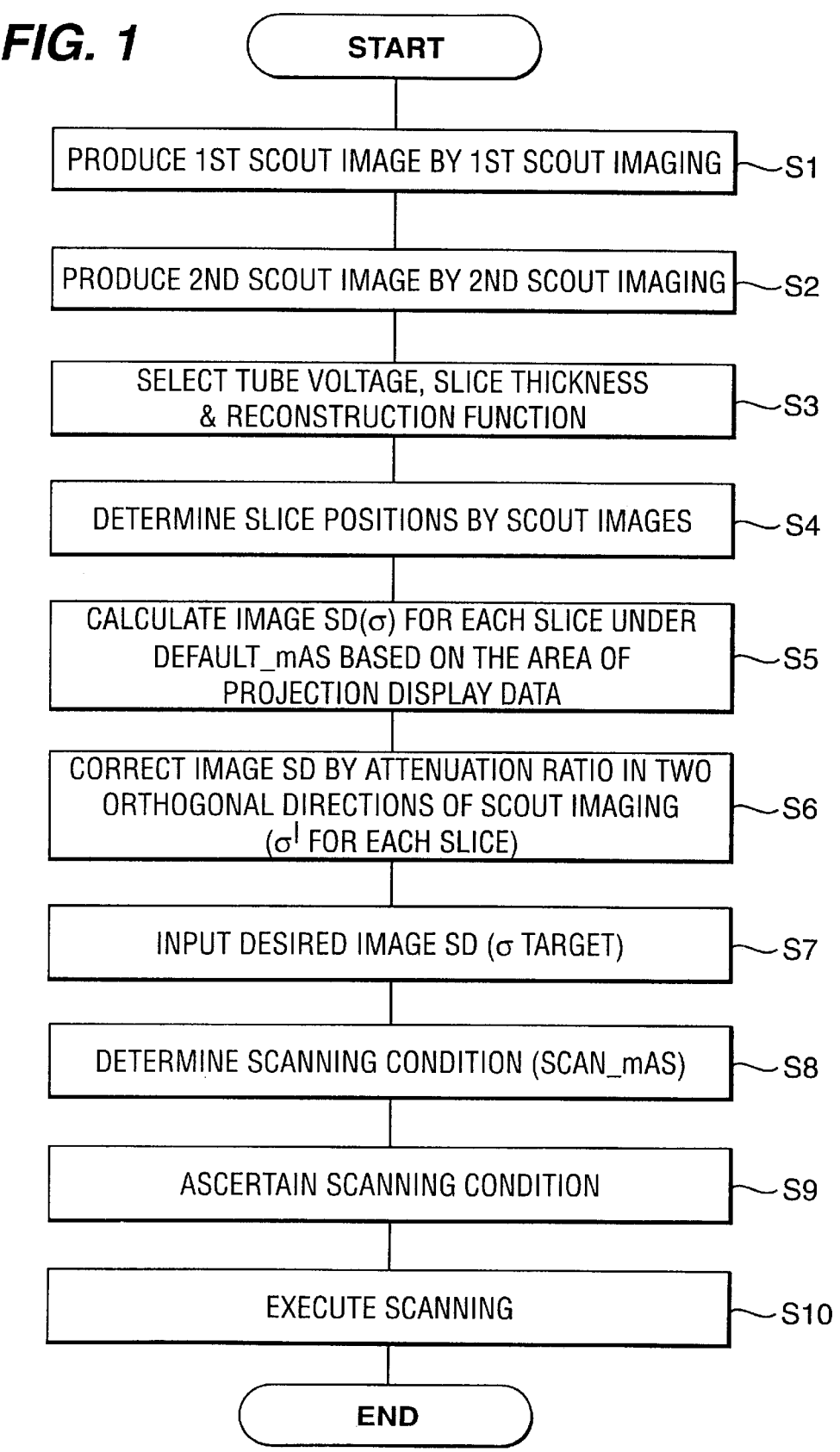
FIG. 1 is a flow chart illustrating an example of processing in an x-ray computed tomography method in accordance with one embodiment of the present invention.
Figure 3:
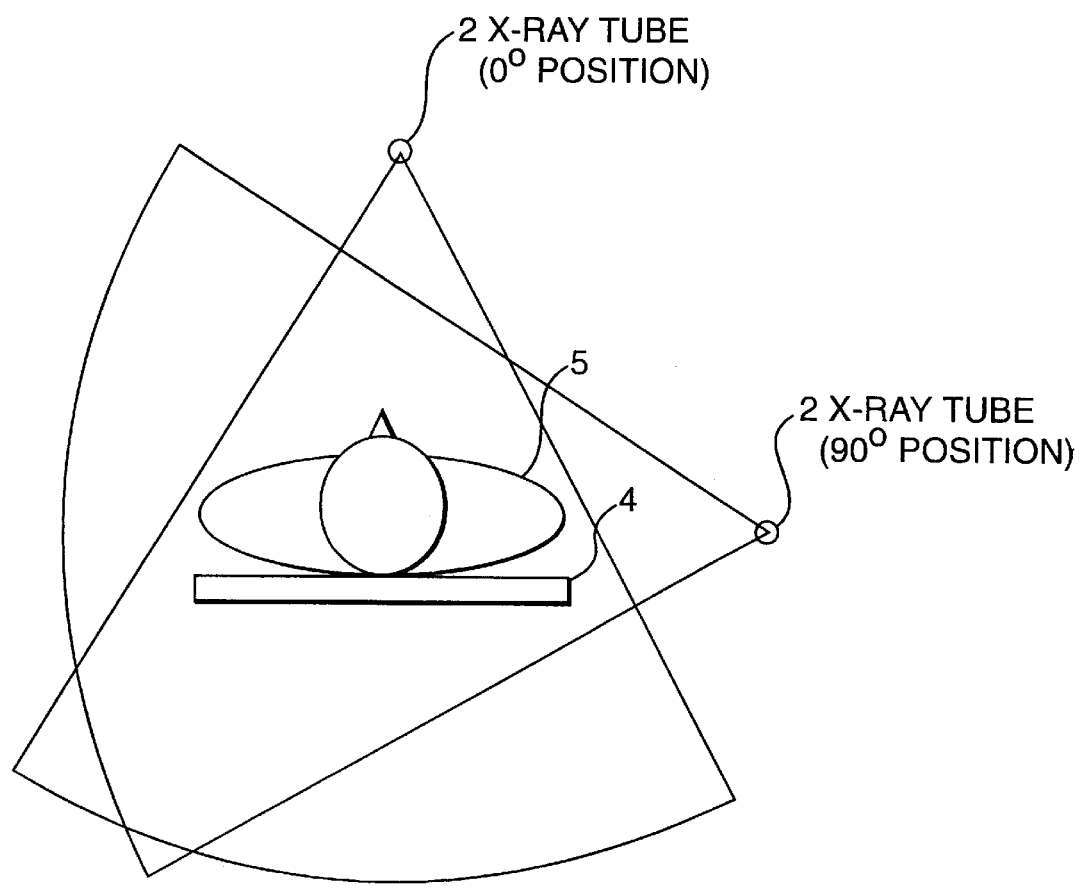
FIG. 3 is an explanatory view in performing the scout imaging in accordance with one embodiment of the present invention.

A first scout image is initially produced by the first scout imaging (S1 in FIG. 1). As shown in FIG. 3, two directions orthogonal to each other are selected as the direction of the scout imaging. For example, the x-ray tube 2 is disposed at 0° position (straight above the subject) and the detector 3 is disposed at 180° position (straight below the subject), as shown in FIG. 3. While the table 4 is translated in the direction of the body axis (the direction perpendicular to the drawing plane of FIG. 3) with the gantry rotating section fixed as above, the x-rays are emitted and the subject transmission projection data is detected. The first scout image is then produced by the scout image producing section 11.

Next, a second scout image is produced by the second scout imaging (S2 in FIG. 1). As shown in FIG. 3, the x-ray tube 2 is disposed at 90° position (on one lateral side of the subject) and the detector 3 is disposed at 270° position (on another lateral side of the subject opposite to the x-ray tube). While the table 4 is translated in the direction of the body axis (the direction perpendicular to the drawing plane of FIG. 3) with the gantry rotating section fixed as above, the x-rays are emitted and the subject transmission projection data is detected. The second scout image is then produced by the scout image producing section 11.

On the assumption that the scout images are thus produced in many directions, the first and second scout images are desirably selected among these scout images so that a scout image which is expected to have the largest maximum pixel value is selected as one scout image and another scout image which is expected to have the smallest maximum pixel value is selected as another scout image.

If the subject has a flat cross section as shown in FIG. 3, the scout images are desirably taken from two directions orthogonal to each other, for example, at 0° direction and 90° direction (or 270° direction). Such scout imaging enables correction of the standard deviation by the attenuation ratio, which will be described later.

[Initialization]

Now the operator performs the initialization for the x-ray computed tomography, such as the selection of the tube voltage, the slice thickness and the reconstruction function (S3 in FIG. 1). The several parameters necessary for the x-ray computed tomography are determined by the operator from the operating section 14 in this initialization step. Moreover, the system controller 15 determines the scanning positions (i.e., slice positions) for the x-ray computed tomography with reference to the scout-images produced by the scout image producing section 11 (S4 in FIG. 1).

[Determination of the Scanning Condition by the Standard Deviation]

(1) Calculation of the Image SD (S5 in FIG. 1)

The standard deviation of the image data (referred to as "image SD") will be hereinafter denoted as σ. The relationship between the area of projection display data ("projection area") of a subject (a human body or a material equivalent to a human body) which is imaged under the default imaging condition, and the image SD $\sigma_{pixel}$ is given as follows:

$$\sigma_{pixel} = f(\text{projection area}),$$

wherein the area of the projection display data can be roughly obtained from the scout image, and 'f' is a predetermined function. This image SD is obtained on the assumption that the subject has a circular cross section. Instead of using the area of the projection display data which is derived as a display image, the area of transmission projection data which is obtained immediately after preprocessing may be employed.

Some values for the image SD $\sigma_{pixel}$ are stored in the form of function or table beforehand to determine the image SD for each slice according to the area of the projection display data derived from the scout image.

(2) Correction of the Image SD (S6 in FIG. 1)

The image SD for each slice obtained from (1) is then corrected according to the attenuation ratio between the scout images in two orthogonal directions. Thus, an image SD σ' corresponding to the subject's actual cross-sectional shape is obtained for each slice.

The image SD $\sigma'_{pixel}$ can be calculated from σ and the attenuation ratio according to the following equations:

$$\sigma'_{pixel} = \sigma_{pixel} \times g(\text{projectionMax\_90°}/\text{projectionMax\_0°},) \text{ when projectionMax\_90°} > \text{projectionMax\_0°},$$

and $$\sigma'_{pixel} = \sigma_{pixel} \times g(\text{projectionMax\_0°}/\text{projectionMax\_90°}) \text{ when projectionMax\_0°} > \text{projectionMax\_90°},$$

wherein projectionMax_0° is the maximum pixel value obtained from the scout imaging at 0°, and projectionMax_90° is the maximum pixel value obtained from the scout imaging at 90°. Their ratio is the attenuation ratio.

Additionally, 'g' is a function of the first order or slightly higher order such as second or third, and the image SD σ' which corresponds to the subject's cross-sectional shape can be obtained from σ in a circular cross section and the attenuation ratio of the subject in the scout imaging. Instead of the pixel values, transmission projection data values may be used.

(3) Determination of the Scanning Condition

It is known that the image SD generally has the following relationship with the imaging condition (i.e., mAs: the product of tube current and time):

$$\sigma_{target}/\sigma'_{pixel} = (\text{default\_mAs}/\text{scan\_mAs})^{1/2}.$$

Therefore, by specifying a desired image SD value as $\sigma_{target}$ (S7 in FIG. 7), the scanning condition 'scan_mAs' which meets $\sigma_{target}$ can be obtained for each slice from $\sigma'_{pixel}$ and the default imaging condition 'default_mAs' (S8 in FIG. 7).

The imaging condition 'scan_mAs' thus obtained is then displayed on the display device 20 etc. by the system controller 15 and the operator ascertains whether the value is appropriate (S9 in FIG. 7). When the confirmation is made, the scanning plan is completed and the process turns to "wait state" for the scanning execution.

[Scanning Execution]

Based on the parameters determined by the above specification and calculation, the x-ray computed tomography scanning is performed (S10 in FIG. 1). That is, the gantry rotating section starts to rotate and simultaneously x-ray emission is turned on, and the x-rays emanate from the x-ray tube 2.

The x-rays are emitted based on the imaging condition 'scan_mAs' obtained so that the image SD $\sigma_{target}$ is met for each slice as described above.

The scan data is then acquired by the detector 3. Based on the data thus acquired, the image reconstructor 11 performs the image reconstruction to produce image data which is displayed on the display device 20 and simultaneously stored in the data storage device 12.

<Effect Obtained from the Embodiment>

(1) The standard deviation σ of the image data based on the area of the projection display data, and the pixel value attenuation ratio between the scout images acquired respectively at the two angular positions of the x-ray source give the standard deviation σ' of the image data under the scanning condition 'default_mAs' prescribed as a default value. And the standard deviation σ and a desired standard deviation $\sigma_{target}$ give a scanning condition 'scan_mAs' required to attain the desired standard deviation.

As a result, the scanning condition for each slice can be controlled so that the standard deviation of the image data is equal to $\sigma_{target}$, which enables the ranges of dispersion in pixel value for several slices to be contained within the same preferred range.

(2) For the scout images taken in two directions for use in determining the scanning condition, since the directions of scout imaging in which the respective maximum pixel values in the scout images are expected to be the largest and smallest values are selected as the two directions, the standard deviation σ' of the image data for the actual subject can be accurately calculated using the standard deviation σ of the image data based on the area of the projection display data, and the attenuation ratio.

As a result, the scanning condition for each slice can be controlled so that the standard deviation of the image data is equal to a desired value, which enables the ranges of dispersion in pixel value for several slices to be contained within the same preferred range.

(3) For the scout images taken in two directions for use in determining the scanning condition, since the two directions of scout imaging are selected to be the sagittal and coronal directions in which the respective maximum pixel values in the scout images are expected to be the largest and smallest values, the standard deviation σ' of the image data for the actual subject can be accurately calculated using the standard deviation σ of the image data based on the area of the projection display data, and the attenuation ratio.

As a result, the scanning condition for each slice can be controlled so that the standard deviation of the image data is equal to a desired value, which enables the ranges of dispersion in pixel value for several slices to be contained within the same preferred range.

Many widely different embodiments of the invention may be configured without departing from the spirit and the scope of the present invention. It should be understood that the present invention is not limited to the specific embodiments described in the specification, except as defined in the appended claims.

What is claimed is:

1. An x-ray computed tomography method in which x-rays emitted from an x-ray source impinges upon a subject placed within a measured volume and the transmitted x-rays are detected by an array of x-ray detector elements, the method comprising the steps of:

prior to the tomographic imaging of the subject, producing scout images by fixing the angular position of the x-ray source at two different angular positions and performing the scout imaging of the subject respectively at the angular positions;

calculating a scanning condition with reference to the standard deviation of image data based on the area of projection display data, a desired standard deviation of the image data and the pixel value attenuation ratio between the scout images acquired respectively at the two angular positions of the x-ray source; and performing the tomographic imaging of the subject according to the scanning condition.

2. An x-ray computed tomography apparatus comprising:

an x-ray source for emitting x-rays toward a subject;

an x-ray detector for detecting subject transmission information of the emitted x-rays; and control means for controlling the x-ray emission and detection, the control means exerts the control so as to, prior to the tomographic imaging of the subject, produce scout images by fixing the angular position of the x-ray source at two different angular positions and performing the scout imaging of the subject respectively at the angular positions, calculates a scanning condition with reference to the standard deviation of image data based on the area of projection display data, a desired standard deviation of the image data and the pixel value attenuation ratio between the scout images acquired respectively at the two angular positions of the x-ray source, and exerts the control so as to perform the tomographic imaging of the subject according to the scanning condition.

3. The x-ray computed tomography apparatus of claim 2, wherein the control means fixes the x-ray source at angular positions so that the respective maximum pixel values in the scout images acquired respectively at the angular positions of the x-ray source are expected to be the largest and smallest values.

4. The x-ray computed tomography apparatus of claim 3, wherein one of the angular positions of the x-ray source at which the maximum pixel value of the scout image is the largest value is selected to be in a direction parallel to the sagittal plane, and the other of the angular positions of the x-ray source at which the maximum pixel value of the scout image is the smallest value is selected to be in a direction parallel to the coronal plane.

* * * * *